(12) United States Patent
Rahman et al.

(10) Patent No.: US 8,789,406 B2
(45) Date of Patent: Jul. 29, 2014

(54) EXHAUST GAS SAMPLING AND ANALYSIS SYSTEM

(75) Inventors: Montajir Rahman, Otsu (JP); Takeshi Kusaka, Omihachiman (JP); Leslie Hill, Kenilworth (GB)

(73) Assignee: Horiba, Ltd., Kyoto (JP)

( * ) Notice: Subject to any disclaimer, the term of this patent is extended or adjusted under 35 U.S.C. 154(b) by 352 days.

(21) Appl. No.: 13/388,198

(22) PCT Filed: Jul. 27, 2010

(86) PCT No.: PCT/JP2010/062641
§ 371 (c)(1),
(2), (4) Date: Jan. 31, 2012

(87) PCT Pub. No.: WO2011/013676
PCT Pub. Date: Feb. 3, 2011

(65) Prior Publication Data
US 2012/0125080 A1 May 24, 2012

(30) Foreign Application Priority Data
Jul. 31, 2009 (JP) .................................. 2009-178832

(51) Int. Cl.
*G01N 7/00* (2006.01)
(52) U.S. Cl.
USPC ........................................................ 73/23.31
(58) Field of Classification Search
CPC .................................................. G01N 1/2252
USPC ................... 73/23.31, 23.32, 23.33
See application file for complete search history.

(56) References Cited

U.S. PATENT DOCUMENTS

| | | | |
|---|---|---|---|
| 2004/0191130 A1* | 9/2004 | Marek et al. | 422/109 |
| 2004/0226354 A1* | 11/2004 | Schmidt | 73/118.1 |
| 2010/0000339 A1* | 1/2010 | Silvis et al. | 73/863.01 |

FOREIGN PATENT DOCUMENTS

| | | |
|---|---|---|
| CN | 1573312 A | 2/2005 |
| JP | 62157546 A | 7/1987 |
| JP | 02-43640 A | 3/1990 |
| JP | 1990043640 U | 3/1990 |
| JP | 02190740 A | 7/1990 |
| JP | 04216435 A | 8/1992 |
| JP | 09318572 A | 12/1997 |
| JP | 10206310 A | 8/1998 |
| JP | 2005106452 A | 4/2005 |
| JP | 2006275983 A | 10/2006 |

* cited by examiner

*Primary Examiner* — Hezron E Williams
*Assistant Examiner* — David Z Huang
(74) *Attorney, Agent, or Firm* — Brooks Kushman P.C.

(57) ABSTRACT

An exhaust gas sampling and analysis system includes a main flow channel in which a flow restriction mechanism and a first suction pump are arranged; a measurement flow channel in which an exhaust gas analysis device is provided and that extends from the main flow channel at a position downstream of the flow restriction mechanism; and a compensation flow channel in which a flow rate adjustment mechanism is provided and that extends from the main flow channel at a position downstream of the point from which the measurement flow channel extends. The first suction pump further reduces the pressure of the exhaust gas. The flow rate adjustment mechanism adjusts, in order that the pressure of the exhaust gas at the point from which the measurement flow channel extends is a predetermined value, the flow rate of the compensation gas.

4 Claims, 4 Drawing Sheets

EXHAUST GAS SAMPLING AND ANALYSIS SYSTEM

CROSS-REFERENCE TO RELATED APPLICATION

This application is the U.S. national phase of PCT Appln. No. PCT/JP2010/062641 filed Jul. 27, 2010, which claims priority to Japanese application JP 2009-178832 filed Jul. 31, 2009, the disclosures of which are incorporated in their entirety by reference herein.

FIELD OF THE ART

This invention relates to an exhaust gas sampling and analysis system that samples an exhaust gas of an engine and analyzes a component of the sampled exhaust gas.

BACKGROUND ART

As shown in the patent document 1, this kind of an exhaust gas sampling and analysis system circulates a diluted exhaust gas that is an exhaust gas from an internal combustion engine (an engine) diluted with air in a dilution pipe and collects a part of the diluted exhaust gas flowing in the dilution pipe by the use of a sample collection pipe.

A sample collection probe to collect the diluted exhaust gas, a flow restriction valve to adjust a flow rate pressure of the collected diluted exhaust gas, an exhaust gas analysis device to analyze a component of the exhaust gas from the diluted exhaust gas, a critical venturi arranged to suck the dilution gas in the sample collection pipe at a constant total amount, and a suction pump are arranged in this order in the sample collection pipe. In addition, an atmospheric air path is connected between the exhaust gas analysis device and the critical venturi in the sample collection pipe. This arrangement makes it possible to reduce a change of a flow pressure of the diluted exhaust gas passing the exhaust gas analysis device in accordance with a ratio between an amount of the diluted exhaust gas flowing in the sample collection pipe and an amount of the atmospheric air introduced from the atmospheric air path.

However, since the total amount of the flow rate of the dilution gas in the sample collection pipe is made constant by means of the critical venturi and the suction pump, there is a problem that the flow rate of the sampled exhaust gas definitely changes if the flow rate of the atmospheric air flowing in the sample collection pipe supplied from the atmospheric air path changes. In addition, if the exhaust gas is of high pressure, the change of the flow rate becomes big. As a result, there is a problem that it is unable for the above-mentioned arrangement to cope with the change of the flow rate.

In addition, for the exhaust gas analysis device used for the exhaust gas sampling and analysis system, since a flow rate and a pressure of the sampled exhaust gas introduced into the exhaust gas analysis device are determined by a specification, it is necessary to adjust the flow rate and the pressure of the sampled exhaust gas within a range of the specification.

In order to attain this object, a pump of a constant volume type is arranged in the downstream side in a flow of the diluted exhaust gas for the exhaust gas sampling and analysis system of the above-mentioned patent document 1 and it is so configured that the total amount and the pressure of the diluted exhaust gas flowing in the dilution pipe are kept generally at a constant value respectively by means of the pump of the constant volume type even though the amount of the exhaust gas flowing in the exhaust gas introduction pipe changes. In addition, an air introduction pipe is connected to the dilution pipe and an air filter is arranged on an atmospheric air take-in port of the air introduction pipe.

However, as is clear from that the total amount and the pressure of the diluted exhaust gas flowing in the dilution pipe are kept generally at a constant value by the use of the pump of the constant volume type for the above-mentioned exhaust gas sampling and analysis system, it is not foreseen to sample the high pressure exhaust gas. In addition, since the air introduction pipe is connected to the dilution pipe and the filter is arranged on the atmospheric air take-in port, it is quite unlikely that the pressure in the dilution pipe becomes high, even though it is likely that the pressure in the dilution pipe becomes low due to clogging of the air filter.

PRIOR ART DOCUMENT

Patent Document

Patent document 1: Japanese unexamined patent application publication number 4-216435

DISCLOSURE OF THE INVENTION

Problems to be Solved by the Invention

The present claimed invention intends to solve all of the problems and a main object of this invention is to analyze a component of an exhaust gas without a reduction in measurement accuracy by sampling an exhaust gas of high pressure.

Means to Solve the Problems

More specifically, the exhaust gas sampling and analysis system in accordance with this invention comprises a main flow channel whose proximal end is connected to an introduction port in order to introduce an exhaust gas, a first suction pump connected to the main flow channel in order to introduce the exhaust gas into the main flow channel, a flow restriction mechanism arranged on the main flow channel, a measurement flow channel that extends from the main flow channel in the downstream of the flow restriction mechanism and that samples and circulates the exhaust gas flowing in the main flow channel, an analysis device that is arranged on the measurement flow channel and that analyzes the sampled exhaust gas, a compensation flow channel that extends from the main flow channel in the downstream of a point from which the measurement flow channel extends and that supplies the main flow channel with a compensation gas, and a flow rate adjustment mechanism that is arranged on the compensation flow channel and that adjusts a flow rate of the compensation gas to be supplied to the main flow channel, and is characterized by that the first suction pump further depressurizes the pressure of the exhaust gas having a pressure which is depressurized when the exhaust gas passes through the flow restriction mechanism to a predetermined value, and the flow rate adjustment mechanism adjusts the flow rate of the compensation gas supplied to the main flow channel so as to make the pressure of the exhaust gas at the point from which the measurement flow channel extends at a predetermined value.

In accordance with this arrangement, since the pressure of the exhaust gas depressurized by the flow restriction mechanism is further depressurized and the pressure of the exhaust gas at the point from which the measurement flow channel extends is made at the predetermined value by adjusting the compensation gas supplied to the main flow channel, it is possible to make the pressure and the flow rate of the exhaust gas flowing in the measurement flow channel within a range of the specification of the analysis device. As a result of this, it is possible to analyze the exhaust gas without a reduction of the measurement accuracy by sampling the exhaust gas flowing at a high pressure in the pipe.

In order to make this effect more remarkable, it is preferable that the introduction port is arranged in the upstream side of a filter device arranged in an exhaust pipe. Although the upstream of the filter device (for example, DPF) occasionally becomes at a high pressure (for example, 300 kPa (gauge pressure)) due to clogging of the filter, it is possible for the exhaust gas sampling and analysis system to sample and analyze the exhaust gas in the upstream of the filter device. As a result of this, if the exhaust gas in the downstream of the filter device is additionally sampled and analyzed and the analysis result in the downstream side 0 and the analysis result in the upstream side are compared, it is possible to evaluate a performance of the filter device.

In order to make it easy to introduce the exhaust gas into the measurement flow channel, it is preferable that an upstream side opening of a pipe constituting the measurement flow channel is arranged to face the upstream side on the same axis as that of the main flow channel, and a constant speed sampling is conducted by a pipe constituting the measurement flow channel. The constant speed sampling is to conduct sampling in a state that a flow velocity of the exhaust gas in the main flow channel and a flow velocity of the exhaust gas in the measurement flow channel are identical. With this arrangement, it is possible to suck a particle having a big diameter without a loss.

In order to make the flow rate variable based on the pressure of the exhaust gas input in the flow restriction mechanism and to make not to lose the component of the particle matters contained in the exhaust gas in the flow restriction mechanism, it is preferable that the flow restriction mechanism comprises a movable body where a main flow restriction channel connected through the main flow channel is formed along an axial line in a center part of the movable body and a single or a plurality of side flow restriction channels are formed along the axial line around the main flow restriction channel, a fixing part that fits over an outer circumference of the movable body in the downstream side in a slidable manner and that closes or opens the side flow restriction channel, and a spring that is arranged between the fixing part and the movable body in the outer circumference of the movable body and that urges the movable body in a direction of being separated from the fixing part, and that a flow rate of the exhaust gas passing in the flow channel is adjusted by a sliding movement of the movable body in the axial direction in accordance with a pressure of the exhaust gas received by the movable body.

Effect of the Invention

In accordance with this invention having the above-mentioned arrangement, it is possible to analyze the component of the exhaust gas without a reduction of the measurement accuracy by sampling the high-pressure exhaust gas.

EXPLANATION OF CODES

Figure 1:
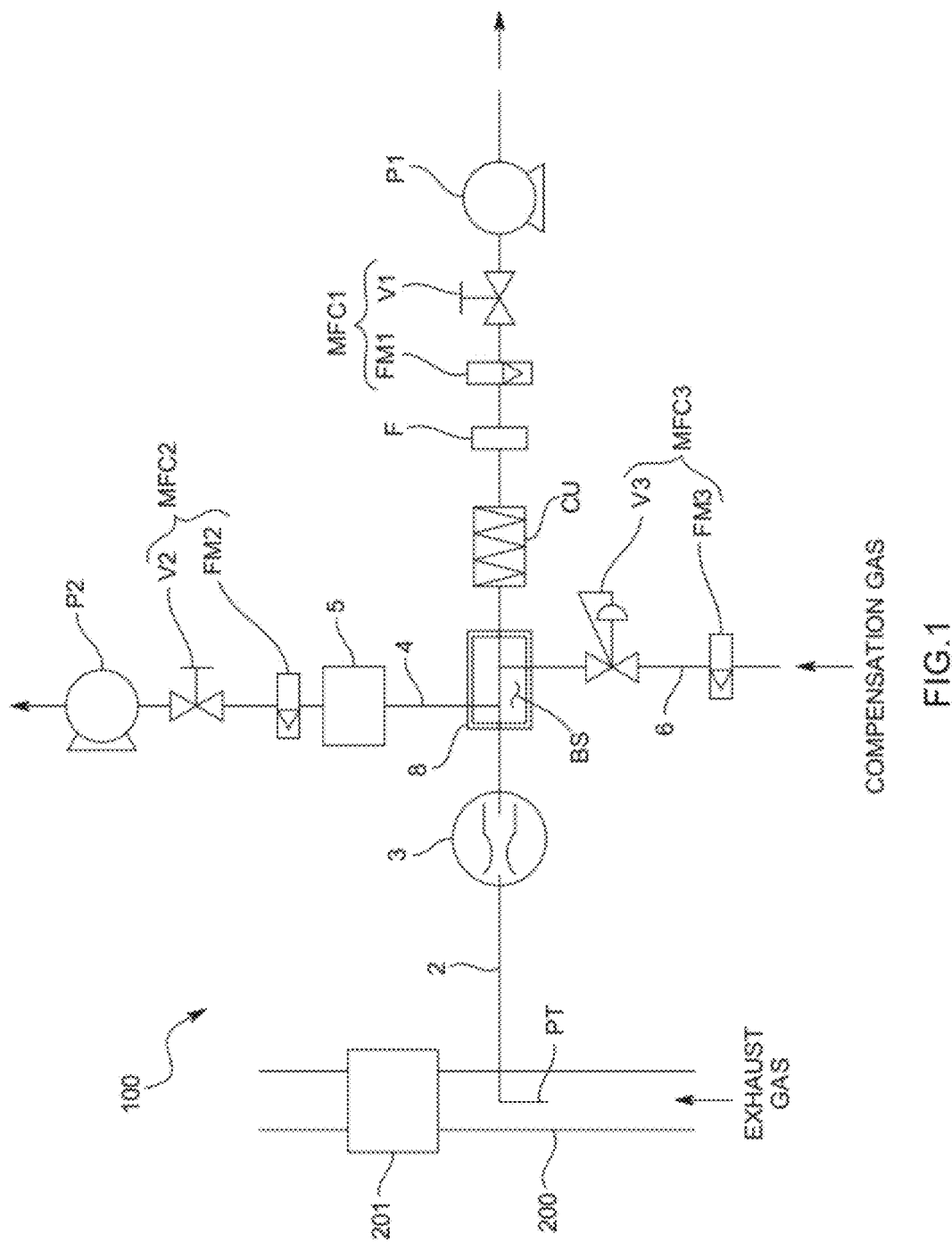
FIG. 1 is a pattern configuration diagram of an exhaust gas sampling and analysis system in accordance with one embodiment of this invention.

100 . . . exhaust gas sampling and analysis system
201 . . . filter device (DPF)
PT . . . introduction port
2 . . . main flow channel
3 . . . flow restriction mechanism
P1 . . . first suction pump
4 . . . measurement flow channel
5 . . . analysis device
6 . . . compensation flow channel
MFC3 . . . flow rate adjustment mechanism
31 . . . movable body
301 . . . main flow restriction channel
302 . . . side flow restriction channel
32 . . . fixing part
33 . . . spring

BEST MODES OF EMBODYING THE INVENTION

An embodiment of an exhaust gas sampling and analysis system 100 in accordance with this invention will be explained with reference to drawings.

The exhaust gas sampling and analysis system 100 in accordance with this embodiment samples an exhaust gas flowing in an exhaust pipe 200 connected to an internal combustion engine (an engine) and analyzes the sampled exhaust gas.

Concretely, the exhaust gas sampling and analysis system 100 comprises, as shown in FIG. 1, a main flow channel 2 whose proximal end is connected to an introduction port (PT) to introduce the exhaust gas, a first suction pump (P1) connected to the main flow channel 2 in order to introduce the exhaust gas into the main flow channel 2, a flow restriction mechanism 3 arranged on the main flow channel 2, a measurement flow channel 4 that extends from the main flow channel 2 in the downstream of the flow restriction mechanism 3 and that samples and circulates the exhaust gas flowing in the main flow channel 2, an exhaust gas analysis device 5 that is arranged on the measurement flow channel 4 and that analyzes the sampled exhaust gas, a compensation flow channel 6 that extends from the main flow channel 2 in the downstream of a point from which the measurement flow channel 4 extends and that supplies the main flow channel 2 with a compensation gas, and a flow rate adjustment mechanism (MFC3) that is arranged on the compensation flow channel 6 and that adjusts a flow rate of the compensation gas to be supplied to the main flow channel 2. In addition, a backflow prevention structure configured to prevent the compensation gas that is supplied by the compensation flow channel 6 from flowing in the measurement flow channel 4 is arranged on the main flow channel 2 between the point from which the measurement flow channel 4 extends and the point from which the compensation flow channel 6 extends.

Each component will be explained in detail.

The introduction port (PT) is arranged in the upstream side of the filter device 201 such as, for example, a diesel particulate filter (DPF) or the like arranged on the exhaust pipe 200. The pressure of the exhaust gas in the upstream of the filter device 201 becomes at a high pressure (for example, 300 kPa (gauge pressure)) due to a cause such as a clogged filter or the like.

A proximal end of the main flow channel 2 is connected to the introduction port (PT), and the flow restriction mechanism 3 comprising a venturi or an orifice, a buffer space (BS) to buffer a pressure fluctuation of the exhaust gas, the first flow rate adjustment mechanism (MFC1), and the first suction pump (P1) are arranged on the main flow channel 2 in this order from the upstream. The first flow rate adjustment mechanism (MFC 1) comprises a flow meter (FM1) and a flow rate adjustment valve (for example, a needle valve) (V1). The flow rate adjustment valve (V1) is controlled by a control part, not shown in drawings, and the control part that receives a flow rate measurement signal from the flow meter (FM1) outputs a control signal to the flow rate adjustment valve (V1) and adjusts an opening ratio of the flow rate adjustment valve (V1). In addition, the first suction pump (P1) is also controlled by the control part and sucks the exhaust gas so as to make a pressure in the downstream (concretely, inside of the buffer space (BS)) of the flow restriction mechanism 3 at a predetermined value. A code (F) in FIG. 1 indicates a filter, and a code (CU) indicates a cooler.

The measurement flow channel 4 is arranged to extend from the main flow channel 2 in the downstream of the flow restriction mechanism 3. A second flow rate adjustment mechanism (MFC2) comprising a flow meter (FM2) and a flow rate adjustment valve (for example, a needle valve) (V2), the analysis device 5 such as, for example, a particle number measurement device (CPC) that analyzes the sampled exhaust gas, and a second suction pump (P2) are arranged on the measurement flow channel 4 in this order from the upstream side (the main flow channel 2 side). The second flow rate adjustment mechanism (MFC2) is controlled by the control part so as to make the flow rate of the exhaust gas flowing in the analysis device 5 at a constant value.

The compensation flow channel 6 is arranged to extend from the main flow channel 2 in the downstream of the point from which the measurement flow channel 4 extends. A third flow rate adjustment mechanism (MFC3) comprising a flow meter (FM3) and a pressure control valve (V3) is arranged on the compensation flow channel 6. A pump to circulate the compensation gas in the compensation flow channel 6 may be arranged. In this embodiment, since the buffer space (BS) is negative pressurized by the first suction pump (P1), it is possible to introduce the compensation gas such as atmospheric air into inside of the buffer space (BS) without providing a pump on the compensation flow channel 6. The pressure control valve (V3) of the third flow rate adjustment mechanism (MFC3) is controlled by the control part so as to make the flow rate of the exhaust gas in the downstream (concretely, inside of the buffer space (BS))) of the flow restriction mechanism 3 at a predetermined value.

A behavior of the exhaust gas sampling and analysis system 100 having the above arrangement will be explained.

Figure 3:
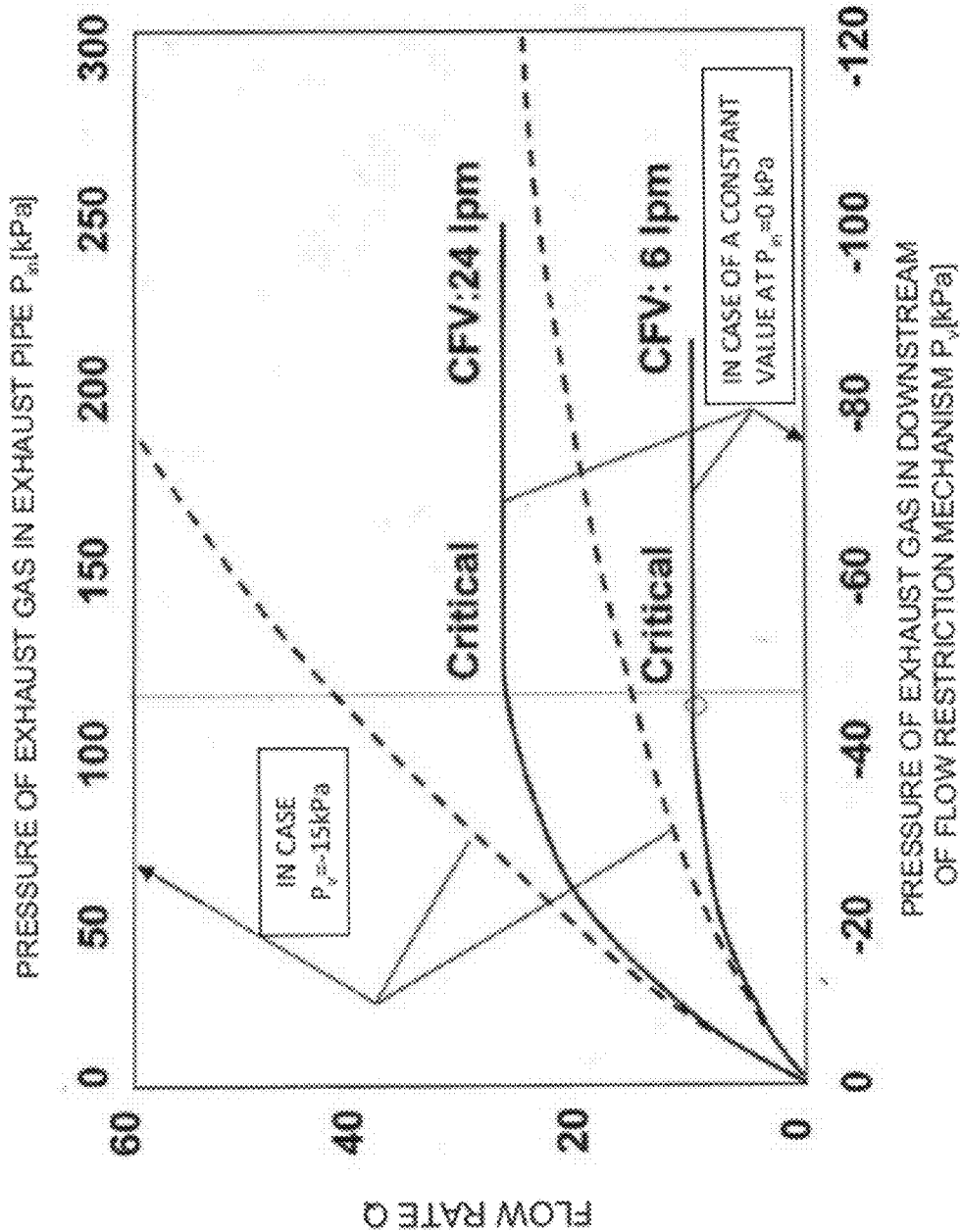
FIG. 3 is a view showing a pressure (a gauge pressure) of a critical venturi—flow rate characteristics.

In case that the pressure in the upstream of the diesel particulate filter 201 of the exhaust pipe 200 is at a high pressure (for example, 300 [kPa] (gauge pressure)), when the exhaust gas is sampled through the introduction port (PT), the pressure of the exhaust gas is reduced (for example, 280 [kPa] (gauge pressure)) due to a venturi (for example, a flow rate performance is 6 [little/minute]) of the flow restriction mechanism 3. The pressure of a critical venturi—the flow rate characteristics is shown in FIG. 3. The pressure in the X axis in FIG. 3 is a gauge pressure. As is clear from FIG. 3, in case that the pressure of the exhaust gas in the downstream of the flow restriction mechanism 3 is constant at −15 [kPa] (gauge pressure), the higher the pressure of the exhaust gas of the exhaust gas pipe 200 is, the less the effect of the pressure reduction due to the venturi becomes. As a result of this, it is not possible to adjust the flow rate of the exhaust gas flowing in the venturi at a constant value so that the flow rate increases. Concretely, in case that the input pressure of the exhaust gas is 300 [kPa] (gauge pressure), the exhaust gas of 20 [little per minute] flows for the flow restriction mechanism 3 (CFV) having a flow rate performance of 6 [little per minute] and the exhaust gas of 100 [little per minute] flows for the flow restriction mechanism 3 (CFV) having a flow rate performance of 24 [little per minute]. Namely, the more the pressure of the exhaust gas of the exhaust pipe 200 rises, the more the flow rate flowing in the flow restriction mechanism 3 (CFV) becomes.

At this time, in order to introduce the exhaust gas into the analysis device 5 by conducting sampling by the measurement flow channel 4, it is necessary to make the pressure and the flow rate in the downstream of the flow restriction mechanism 3 at a predetermined value respectively. At a time when the exhaust gas is sampled by the measurement flow channel 4, the predetermined value is the pressure and the flow rate of the sampled exhaust gas each of which satisfies a measurement specification of the analysis device 5.

Then the exhaust gas is sucked by the first suction pump (P1) so as to make the pressure (for example, 280 [kPa] (gauge pressure)) in the downstream of the flow restriction mechanism 3 at a predetermined value within a predetermined range (for example, −35 kPa~35 kPa (gauge pressure)). As mentioned, if the pressure in the downstream of the flow restriction mechanism 3 is lowered to a value within a predetermined range, the flow rate at the point from which the measurement flow channel 4 extends becomes too big. Then, the compensation gas is supplied to the main flow channel 2 by the compensation flow channel 6. As a result of this, the flow rate of the exhaust gas in the downstream of the flow restriction mechanism 3 becomes smaller so that the flow rate falls within the predetermined range. Accordingly, the pressure of the exhaust gas at the point from which the measurement flow channel 4 extends becomes at a predetermined value within the predetermined range (for example, −35 kPa~35 kPa (gauge pressure)).

Figure 4:
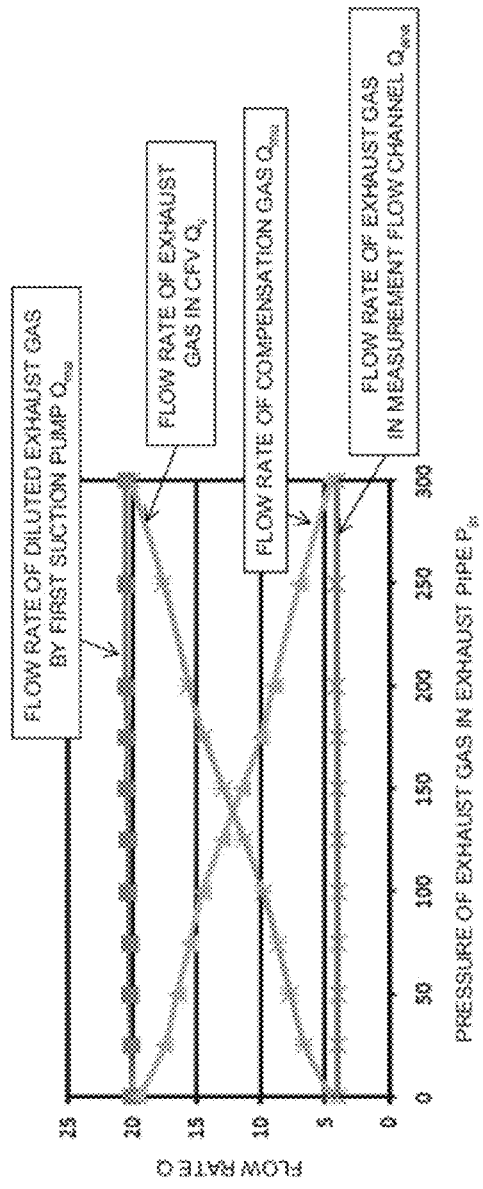
FIG. 4 is a view showing a flow rate characteristics of each part in the exhaust gas sampling and analysis system of this embodiment.
Figure 5:
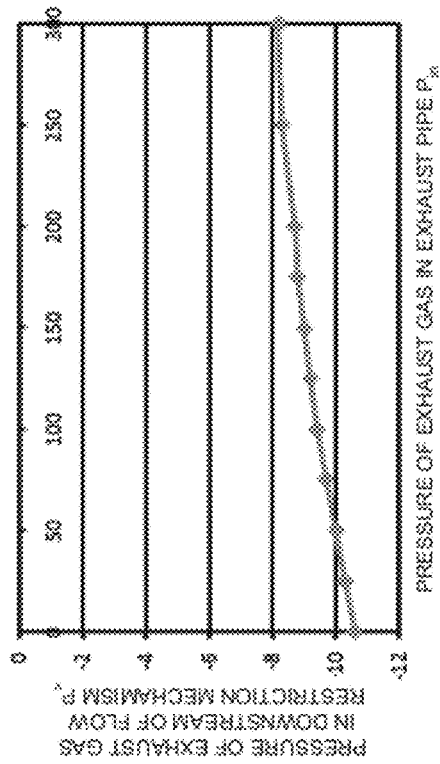
FIG. 5 is a view showing an exhaust gas pressure (a gauge pressure) in the downstream of the flow restriction mechanism in the exhaust gas sampling and analysis system of this embodiment.

A sampling result of the high pressure exhaust gas using the exhaust gas sampling and analysis system 100 of this embodiment will be explained with reference to FIG. 4 and FIG. 5. It is so set that flow rate of a diluted exhaust gas (a flow rate of the exhaust gas diluted by the compensation gas) by the first suction pump (P1) is ($Q_{ma}$), a flow rate of the compensation gas supplied to the main flow channel 2 is ($Q_{mu}$), a flow rate of the exhaust gas flowing in the measurement flow channel 4 is ($Q_{ana}$), a flow rate of the exhaust gas flowing in the flow restriction mechanism 3 (CFV) is ($Q_v$), and a pressure of the exhaust gas in the downstream of the flow restriction mechanism 3 is ($P_v$). In this embodiment used was a flow restriction mechanism 3 (CFV) having a flow rate performance of 5.0 [little per minute]. In addition, each of the pressures shown in FIG. 4 and FIG. 5 is the gauge pressure. Even though the pressure of the exhaust gas to be input is changed within a range of 0~300 [kPa] (gauge pressure)], it is possible to make the flow rate ($Q_{ana}$) of the exhaust gas in the measurement flow channel 4 at about 4.00 [little per minute]

(refer to FIG. 4), and to make the pressure ($P_v$) of the exhaust gas within a range of −10.60~−8.20 [kPa (gauge pressure)] (refer to FIG. 5).

As mentioned, since it is possible to calculate the dilution ratio with high accuracy by improving the flow rate accuracy of the exhaust gas sampled by the measurement flow channel 4 without malfunction of the analysis device 5 due to the exhaust gas sucked by the second suction pump (P2) on the measurement flow channel 4 by making the pressure and the flow rate of the exhaust gas in the downstream of the flow restriction mechanism 3 at the predetermined value, a measurement accuracy of the analysis device 5 can be improved.

Figure 2:
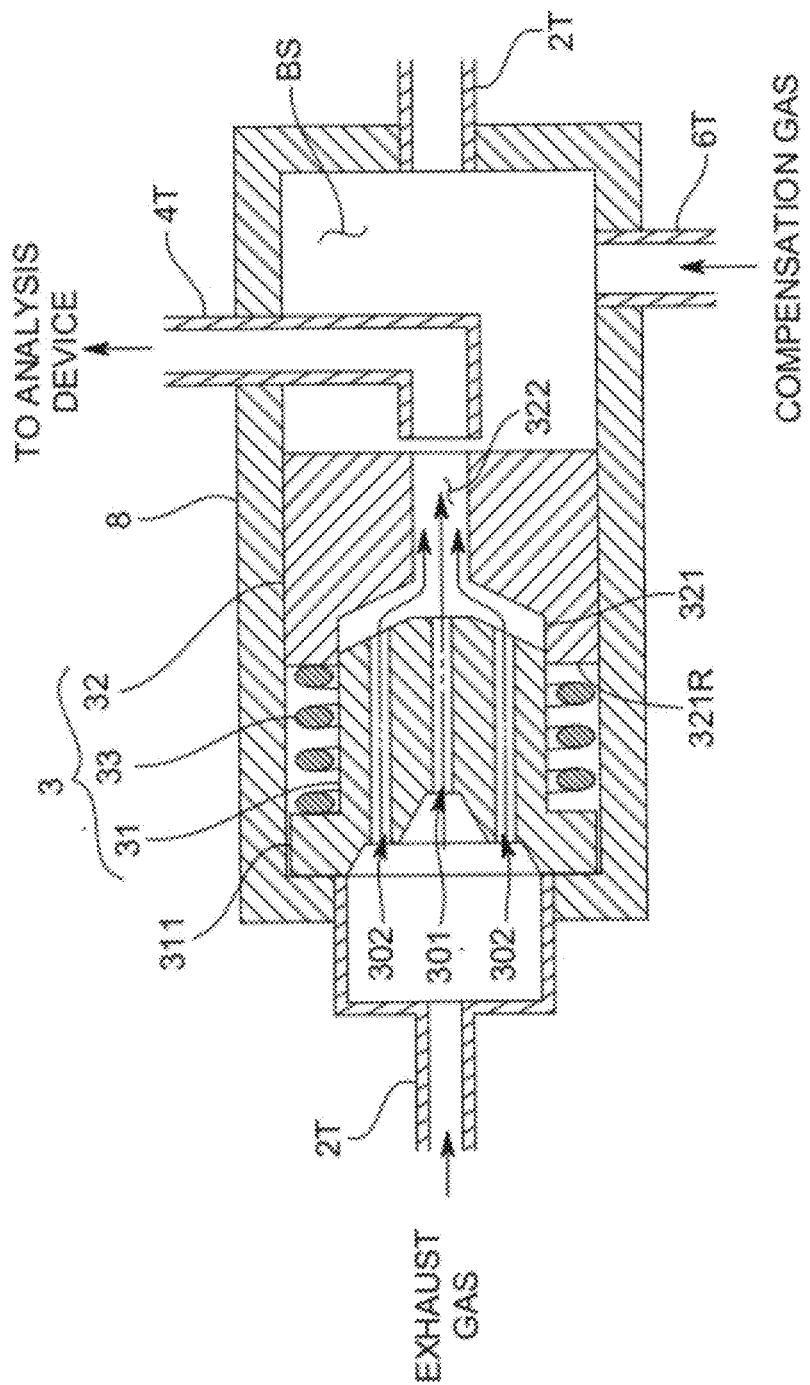
FIG. 2 is a cross-sectional view showing a pattern diagram of a flow restriction mechanism and its peripheral pipe in this embodiment.

The flow restriction mechanism 3 of this embodiment is a flow rate variable venturi, and the venturi 3 is, as shown in FIG. 2, housed in a housing 8 forming a buffer space (BS).

The flow rate variable venturi 3 is so arranged that an area of a flow channel varies due to a pressure of the exhaust gas input to the venturi 3, and comprises a movable body 31 in a shape of a body of rotation for which formed are a main flow restriction channel 301 and a side flow restriction channel 302, a fixing part 32 that fits over an outer circumference of the movable body 31 in the downstream side in a slidable manner and that closes or opens the side flow restriction channel 302, and a spring 33 that is arranged between the fixing part 32 and the movable body 31 in the outer circumference of the movable body 31 and that urges the movable body 31 in a direction of being separated from the fixing part 32.

The movable body 31 is so formed that in a center part of the movable body 31 formed is the main flow restriction channel 301 connected through the main flow channel 2 along an axial line and around the main flow restriction channel 301 formed is a single or a plurality of side flow restriction channels 302 connected through the main flow channel 2 along the axial line to surround the main flow restriction channel 301. The flow channel area of each side flow restriction channel 302 is identical and the flow channel area of the side flow restriction channel 302 is smaller than a flow channel area of the main flow restriction channel 301.

The fixing part 32 is arranged to be fixed to an inner side circumference surface of the housing 8 and comprises a concave part 321 that slidably fits over the downstream side of the movable body 31 and a through bore 322 arranged on a bottom wall of the concave part 321. An opening diameter of the concave part 321 is generally the same as a diameter of an outer circumference in the downstream of the movable body 31 or a little larger than the diameter of the outer circumference thereof. In addition, a bottom surface of the concave part 321 is tapered to correspond to a distal end surface (tapered in this embodiment) where an opening in the downstream side of the side flow restriction channel 302 is formed. The through bore 322 is arranged on the bottom wall of the concave part 321 in the generally same direction as the flow channel direction of the main flow restriction channel 301 of the movable body 31.

In a state that the movable body 311 is seated (at a closed position where the movable body 31 moves in the axial direction and makes contact with the fixing part 32 so that the side flow restriction channels 302 are closed), the side flow restriction channels 302 are closed and the exhaust gas flowing in the main flow restriction channel 301 passes the through bore 322 and flows in the downstream. Meanwhile, in a state that the movable body 31 is separated from the fixing part 32 (at an open position where the movable body 31 moves in the axial direction so as to be separated from the fixing part 32 so that the side flow restriction channels 302 are open), the side flow restriction channels 302 are open and the exhaust gas flowing in the main flow restriction channel 301 and the side flow restriction channel 302 passes the through bore 322 and flows in the downstream. The flow channel cross sectional area of the side flow restriction channel 302 increases or decreases due to a movement of the movable body 31 between the seated position and the separated position.

The spring 33 fits over the movable body 31 and is arranged between a fringe part 311 formed around an entire circumference of a proximal end part of the movable body 31 and a concave circumference part (321R) of the fixing part 32. The fringe part 311 is slidably and fittingly inserted into the inner side circumference surface of the housing 8. In other words, the spring 33 is housed in a space formed by an outer surface of the movable body 31, a side surface of the fringe part 311, the concave circumference part 321R of the fixing part 32 and the inner side circumference surface of the housing 8 so that the spring 33 will not contact the flowing exhaust gas. With this arrangement, it is possible to prevent loss of a component of the particle matters contained in the exhaust gas due to attachment to the spring 33.

The spring 33 expands and contracts in accordance with a pressure of the exhaust gas received by the movable body 31 and determines the flow channel cross-sectional area of the side flow restriction channel 302 in accordance with the pressure of the exhaust gas. With this arrangement, the movable body 31 makes a sliding movement in the axial direction in accordance with the pressure of the exhaust gas received by the movable body 31 so that a flow rate of the exhaust gas passing the side flow restriction channel 302 is adjusted. As a result of this, the flow rate of the exhaust gas passing the venturi 3 is adjusted.

A pipe constituting the measurement flow channel 4 (hereinafter called as "a pipe for measurement (4T)") and a pipe constituting the compensation flow channel 6 (hereinafter called as "a pipe for compensation (6T)") are connected to the buffer space (BS) formed in the downstream of the venturi 3 by the housing 8. Due to the buffer space (BS), it is possible to mitigate a pressure fluctuation due to pulsation of the pressure of the exhaust gas and pulsation of the first suction pump (P1). A code (2T) in FIG. 2 is a pipe constituting the main flow channel 2.

More concretely, the pipe for measurement (4T) is connected in the upstream side of the pipe for compensation (6T) and an upstream side opening of the pipe for measurement (4T) is arranged to face generally the same direction as the flow channel direction of the main flow channel 2. More particularly, the upstream side opening of the pipe for measurement (4T) is arranged to face generally the same direction as the flow channel direction of the main flow restriction channel 301 of the venturi 3. In this embodiment, the upstream side opening of the pipe for measurement (4T) is arranged near a downstream side opening of the flow channel (the through bore 322) formed for the fixing part 32. With this arrangement, it is possible to directly introduce the exhaust gas sampled through the exhaust pipe 200 into the measurement flow channel 4. In addition, a backflow prevention structure to prevent the compensation gas supplied to the main flow channel 2 from the compensation flow channel 6 from flowing in the measurement flow channel 4 is configured by arranging the upstream side opening of the pipe for measurement (4T) near the downstream side opening of the through bore 322.

<Effect of this Embodiment>

In accordance with the exhaust gas sampling and analysis system 100 in accordance with this embodiment having the above arrangement, since the pressure of the exhaust gas depressurized by the flow restriction mechanism 3 is further depressurized and the pressure of the exhaust gas at the point from which the measurement flow channel 4 extends is made at a predetermined value by adjusting the compensation gas supplied to the main flow channel 2, it is possible to make the flow rate of the exhaust gas flowing in the measurement flow channel 4 within a range of the specification of the analysis device 5. As a result of this, it is possible to analyze the exhaust gas without a reduction in the measurement accuracy by sampling the high pressure exhaust gas.

The present claimed invention is not limited to the above-mentioned embodiment.

For example, in the above-mentioned embodiment, the flow restriction mechanism 3 is arranged inside of the housing 8 forming the buffer space (BS), however, the flow restriction mechanism 3 and the housing 8 may be separately arranged on the main flow channel 2.

In addition, the buffer space (BS) is provided in the above-mentioned embodiment, however, the buffer space (BS) may not be provided.

Furthermore, the backflow prevention structure is formed by arranging the upstream side opening of the pipe for measurement (4T) near the downstream side opening of the venturi (the flow restriction mechanism 3), however, the backflow prevention structure may be configured by a resistance formed by an inner surface of the pipe constituting the main flow channel 2.

In addition, the present claimed invention is not limited to the above-mentioned embodiment and may be variously modified without departing from a spirit of the invention.

Possible Applications in Industry

As mentioned, in accordance with this invention, it is possible to analyze a component of an exhaust gas without a reduction in the measurement accuracy by sampling a high-pressure exhaust gas.

The invention claimed is:

1. An exhaust gas sampling and analysis system comprising
    a main flow channel whose proximal end is connected to an introduction port configured to introduce an exhaust gas,
    a first suction pump connected to the main flow channel configured to introduce the exhaust gas into the main flow channel,
    a flow restriction mechanism arranged on the main flow channel,
    a measurement flow channel that extends from the main flow channel in the downstream of the flow restriction mechanism and that samples and circulates the exhaust gas flowing in the main flow channel,
    an analysis device that is arranged on the measurement flow channel and that analyzes the sampled exhaust gas,
    a compensation flow channel that extends from the main flow channel in the downstream of a point from which the measurement flow channel extends and that supplies the main flow channel with a compensation gas, and
    a flow rate adjustment mechanism that is arranged on the compensation flow channel and that adjusts a flow rate of the compensation gas to be supplied to the main flow channel, wherein
    the flow restriction mechanism and the first suction pump depressurizes the pressure of the exhaust gas that passes through the flow restriction mechanism, and
    the flow rate adjustment mechanism adjusts the flow rate of the compensation gas supplied to the main flow channel so as to make the pressure of the exhaust gas at the point from which the measurement flow channel extends at a predetermined value.

2. The exhaust gas sampling and analysis system described in claim 1, wherein
    the introduction port is arranged in the upstream side of a filter device arranged in an exhaust pipe.

3. The exhaust gas sampling and analysis system described in claim 1, wherein
    an upstream side opening of a pipe constituting the measurement flow channel is arranged to face the upstream side on the same axis as that of the main flow channel, and
    a constant speed sampling is conducted by a pipe constituting the measurement flow channel.

4. The exhaust gas sampling and analysis system described in claim 1, wherein
    the flow restriction mechanism comprises
    a movable body where a main flow restriction channel connected through the main flow channel is formed along an axial line in a center part of the movable body and a single or a plurality of side flow restriction channels are formed along the axial line around the main flow restriction channel,
    a fixing part that fits over an outer circumference of the movable body in the downstream side in a slidable manner and that closes or opens the side flow restriction channel, and
    a spring that is arranged between the fixing part and the movable body in the outer circumference of the movable body and that urges the movable body in a direction of being separated from the fixing part, wherein
    a flow rate of the passing exhaust gas is adjusted by a sliding movement of the movable body in the axial direction in accordance with a pressure of the exhaust gas received by the movable body.

* * * * *